United States Patent
Ko et al.

(10) Patent No.: US 9,439,432 B2
(45) Date of Patent: Sep. 13, 2016

(54) PHENYLISOXAZOLINE-BASED COMPOUND HAVING HERBICIDAL ACTIVITY AND USE THEREOF

(75) Inventors: Young Kwan Ko, Daejeon (KR); Gyu Hwan Yon, Daejeon (KR); Jae Wook Ryu, Daejeon (KR); Dong Wan Koo, Daejeon (KR); Jun Ho Nam, Daejeon (KR); Sung Wan Pyo, Daejeon (KR); Jae Min Hwang, Daejeon (KR); Suk Jin Koo, Daejeon (KR); Ki Hwan Hwang, Daejeon (KR); Dong Guk Lee, Daejeon (KR); Man Seok Jeon, Daejeon (KR); Nam Gyu Cho, Daejeon (KR); Sung Hun Kim, Daejeon (KR); Jong Su Lim, Daejeon (KR); Kun Hoe Chung, Daejeon (KR)

(73) Assignees: MOGHU RESEARCH CENTER LTD, Daejeon (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 14/349,327

(22) PCT Filed: May 18, 2012

(86) PCT No.: PCT/KR2012/003973
§ 371 (c)(1),
(2), (4) Date: Apr. 2, 2014

(87) PCT Pub. No.: WO2013/051776
PCT Pub. Date: Apr. 11, 2013

(65) Prior Publication Data
US 2014/0256553 A1    Sep. 11, 2014

(30) Foreign Application Priority Data
Oct. 4, 2011  (KR) .................. 10-2011-0100842

(51) Int. Cl.
*A01N 43/80* (2006.01)
*C07D 261/04* (2006.01)

(52) U.S. Cl.
CPC ............. *A01N 43/80* (2013.01); *C07D 261/04* (2013.01)

(58) Field of Classification Search
None
See application file for complete search history.

(56) References Cited

U.S. PATENT DOCUMENTS

| 4,983,210 A * | 1/1991 | Rheinheimer et al. ........ 504/248 |
| 5,262,388 A | 11/1993 | Munro et al. |
| 6,838,416 B2 | 1/2005 | Ryu et al. |
| 2004/0110749 A1 | 6/2004 | Nakatani et al. |
| 2008/0318784 A1 * | 12/2008 | Koo et al. .................... 504/138 |

FOREIGN PATENT DOCUMENTS

| JP | 1997-143171 A | 12/1998 |
| JP | 2001-158787 A | 6/2001 |

OTHER PUBLICATIONS

International Search Report for PCT/KR2012/003973.
Lee JN et al., 2007. Mode of action of a new isoxazoline compound. Proc. 21st APWSS Conf. p. 597-601, Colombo, Sri Lank.

* cited by examiner

*Primary Examiner* — Mina Haghighatian
*Assistant Examiner* — Erin Hirt
(74) *Attorney, Agent, or Firm* — The PL Law Group, PLLC

(57) ABSTRACT

Provided are an ortho-substituted phenylisoxazoline-based compound with 2,6-difluorobenzyloxymethyl represented by Formula 1, or a racemate or enantiomer thereof, a herbicide including the ortho-substituted phenylisoxazoline-based compound, or the racemate or enantiomer thereof as an active ingredient, and a method of selectively controlling grass weed comprising treating with the ortho-substituted phenylisoxazoline-based compound, or the racemate or enantiomer thereof before or after the grass weed emerges.

18 Claims, No Drawings

PHENYLISOXAZOLINE-BASED COMPOUND HAVING HERBICIDAL ACTIVITY AND USE THEREOF

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2012/003973, filed May 18, 2012, which claims priority to Korean Patent Application No. 10-2011-0100842, filed Oct. 4, 2011, entire contents of which are incorporated herein by reference.

BACKGROUND

1. Technical Field

The present invention relates to a phenylisoxazoline-based compound having herbicidal activity and a use thereof, and in particular, to an ortho-substituted phenylisoxazoline-based compound with 2,6-difluorobenzyloxymethyl represented by Formula 1, a racemate or enantiomer thereof, a herbicide including the phenylisoxazoline-based compound, or the racemate or enantiomer thereof as an active ingredient, and a method of selectively controlling grass weed with the phenylisoxazoline-based compound, or the racemate or enantiomer thereof before or after the grass weed emerges.

2. Background Art

In general, weeds control is very important in improving productivity of farming, and various herbicides were developed and used. However, there are still many other weeds causing loss in farming, leading to more research in development of new herbicides with high herbicidal activities and crops selectivity. Regarding a herbicidal active ingredient having an isoxazoline-based chemical structure, U.S. Pat. No. 4,983,210 discloses an isoxazoline compound represented by Formula 2a below:

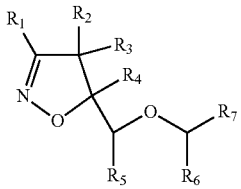

[Formula 2a]

wherein, $R_1$ indicates a $C_1$ to $C_{12}$ alkyl group, a $C_3$ to $C_7$ cycloalkyl group, a substituted or unsubstituted phenyl group, or a saturated or unsaturated 5 to 6-membered heterocyclic group, $R_2$, $R_3$, $R_4$, $R_5$, and $R_6$ each indicates a hydrogen atom, an alkyl group or a benzyl group, and $R_7$ indicates a substituted or unsubstituted $C_2$ to $C_6$ alkenyl, $C_5$ to $C_7$ cycloalkenyl, phenyl, naphthyl, or thienyl.

U.S. Pat. No. 4,983,210 is the first from among inventions relating to the same kinds of compound, and Formula 2a represents any possible compounds thereof. However, within the same scope of patent, only 128 compounds are disclosed with their structures. Regarding biological activities, the patent discloses in its example that at an application rate of 1 kg/ha before weeds emerged, rape showed tolerance, and another example discloses that sunflower had tolerance at an application rate of 0.5 kg/ha at which a herbicidal activity toward weeds was obtained. However, in the latter example, the weeds were not specified. Also, the latter example discloses that at a postemergence application rate of 1 kg/ha, a herbicidal activity was obtained to common lamsquarter (*Chenopodium album*), which is one of broadleaved weeds, without damaging crops (rape and sunflower). However, any effects have not been disclosed on grass weeds, such as barnyardgrass (*Echinochloa crusgalli*) or annual bluegrass (*Poa annua*).

Later this patent, U.S. Pat. No. 5,262,388 disclosed a herbicidal compound having nitrophenylisoxazoline represented by Formula 2b:

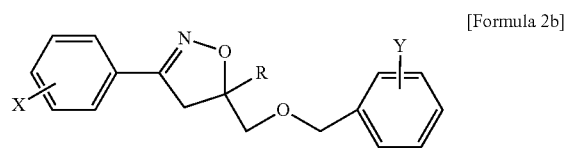

[Formula 2b]

wherein, X indicates a nitro group, Y indicates a hydrogen atom or a halogen group, and R indicates a $C_1$ to $C_6$ alkyl group. The structure of Formula 2b is equivalent to the structure of Formula 2a disclosed in U.S. Pat. No. 4,983,210 in which $R_1$ and $R_7$ are each substituted with a phenyl group, and the structure of Formula 2b is included in the scope of the claims of the preceding patent but not in Examples thereof. The structure of Formula 2b has high effects on barynardgrass (*Echinochloa crusgalli*), which has not been disclosed in the preceding patents.

Japanese Publication Patent No. 1997-143171 discloses an isoxazoline compound represented by Formula 2c below:

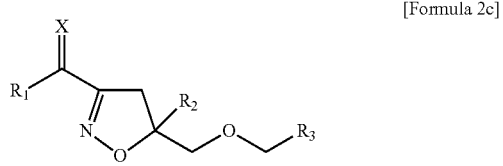

[Formula 2c]

wherein, $R_1$ indicates an alkyl group or an aryl group, X indicates an oxygen or an $NOR_4$ group, $R_2$ indicates an alkyl group, and $R_3$ indicates a substituted aryl group.

Japanese Publication Patent No. 2001-158787 discloses a pyrazole isoxazoline compound represented by Formula 2d below:

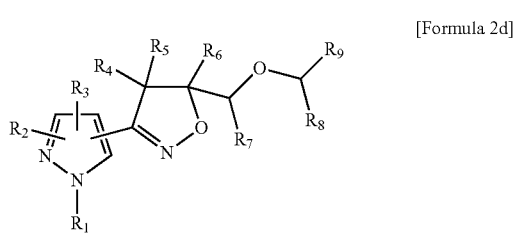

[Formula 2d]

wherein, $R_1$, $R_2$, and $R_3$ each indicates a hydrogen, a halogen group, a nitro group, a cyano group, a hydroxy group, a haloalkyl, or a substituted phenyl, $R_4$, $R_5$, $R_6$, $R_7$, and $R_8$ each indicates a hydrogen, haloalkyl haloalkenyl, or substituted phenyl, and $R_9$ indicates a substituted aryl.

U.S. Pat. No. 6,838,416 discloses a thiophene isoxazoline compound represented by Formula 2e below:

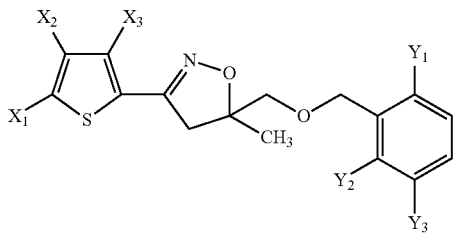

[Formula 2e]

wherein, $X_1$, $X_2$, and $X_3$ each indicates a hydrogen atom, an alkyl group, a halogen group, a methoxy group, or a nitro group, and $Y_1$, $Y_2$, and $Y_3$ each indicates a hydrogen atom or a fluorine atom.

The structures of Formulae 2d and 2e conform to the chemical structure of Formula 2a, but are not included in examples of Formula 2a, and the structures of Formulae 2d and 2e have stability with respect to rice and high effects on *Echinochloa crusgalli*, which is a major weed with respect to rice.

However, the compounds represented by Formulae 2a to 2e have not been used as commercially available chemicals for culturing crops. This is because an amount thereof required is as high as about 1 kg/ha and thus, compared to recently developed other kinds of chemicals, their economical efficiency is low. However, understanding structural activity relationships for the reduction in the use rate is very poor. Meanwhile, in agriculture, emergence of herbicide-resistant weeds is a big issue to be solved, and to control resistant weeds, new kinds of herbicides showing a novel action need to be developed. Isoxazoline-based herbicidal compounds are known to have a different herbicidal action. That is, isoxazoline herbicides are reported to inhibit biosynthesis of a plant cell wall, and their inhibitory manners differ from those of other cell-wall inhibiting agents (Lee J N et al., 2007. Mode of action of a new isoxazoline compound. Proc. 21st APWSS tConf. 597-601, Colombo, Sri Lanka). Accordingly, it is highly likely to develop a novel herbicide for controlling resistant weeds from isoxazoline-based herbicidal compounds. Against this backdrop, inventors of the present invention studied structural activities relationships regarding each substituent of isoxazoline-based herbicidal compounds to develop novel materials with higher herbicidal effects than the materials disclosed in the preceding patents.

SUMMARY

The inventors of the present application confirmed that an ortho-substituted phenylisoxazoline-based compound with 2,6-difluorobenzyloxymethyl represented by Formula 1 selectively controls grass weeds, completing the present invention.

One or more embodiments of the present invention provide an ortho-substituted phenylisoxazoline-based compound with 2,6-difluorobenzyloxymethyl represented by Formula 1, or a racemate or enantiomer thereof.

One or more embodiments of the present invention provide a herbicide including the ortho-substituted phenylisoxazoline-based compound, or the racemate or enantiomer thereof as an active ingredient.

One or more embodiments of the present invention provide a method of selectively controlling grass weed comprising treating with the ortho-substituted phenylisoxazoline-based compound, or the racemate or enantiomer thereof before or after the grass weed emerges.

The phenylisoxazoline-based compound has 4 or more times as high as the herbicidal activity of typical isoxazoline-based compounds, and thus, its stability with respect to major crops, such as bean, corn, cotton, wheat, or rice, is high, and when used, major grass weeds, such as barnyardgrass (*Echinochloa crusgalli*), blackgrass (*Alopecurus myosuroides*), crabgrass (*Digitaria sanguinalis*), or annual bluegrass (*Poa annua*), are effectively controlled. Accordingly, when the phenylisoxazoline-based compound is used, productivity of crops may improve.

DETAILED DESCRIPTION

An aspect of the present invention provides an ortho-substituted phenylisoxazoline-based compound with 2,6-difluorobenzyloxymethyl represented by Formula 1, or a racemate or enantiomer thereof:

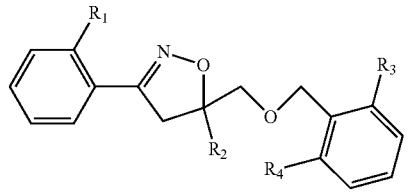

[Formula 1]

wherein, $R_1$ indicates a $C_1$ to $C_4$ alkyl group, a halogen group, or a haloalkyl group, $R_2$ indicates a hydrogen, a methyl group, or an ethyl group, and $R_3$ and $R_4$ each indicates a fluorine. For example, $R_1$ indicates a methyl group, a fluorine group, a chorine group, a bromine group, or a trifluoromethyl group, $R_2$ indicates a hydrogen, a methyl group, or an ethyl group, and $R_3$ and $R_4$ each indicates a fluorine.

For example, the phenylisoxazoline-based compound, or the racemate or enantiomer is selected from
5-((2,6-difluorobenzyloxy)methyl)-5-methyl-3-O-tolyl-4,5-dihydroisoxazole,
3-(2-chlorophenyl)-5-((2,6-difluorobenzyloxy)methyl)-5-methyl-4,5-dihydroisoxazole,
3-(2-bromophenyl)-5-((2,6-difluorobenzyloxy)methyl)-5-methyl-4,5-dihydroisoxazole,
5-((2,6-difluorobenzyloxy)methyl)-3-(2-fluorophenyl)-5-methyl-4,5-dihydroisoxazole, and
5-((2,6-difluorobenzyloxy)methyl)-5-methyl-3-(2-(trifluoromethyl)phenyl)-4,5-dihydroisoxazole.

Another aspect of the present invention provides a herbicide including the phenylisoxazoline-based compound, or the racemate or enantiomer thereof as an active ingredient. For example, the herbicide may include the phenylisoxazoline-based compound, a racemate or enantiomer thereof as a single active ingredient in an amount of 0.5 to 80 wt % based on the final product, but the amount of the phenylisoxazoline-based compound, a racemate or enantiomer thereof is not limited thereto. For example, the herbicide may include the phenylisoxazoline-based compound, a racemate or enantiomer thereof, as an active ingredient of a mixed product, in an amount of 0.5 to 40 wt % based on the final product, but the amount of the phenylisoxazoline-based compound, a racemate or enantiomer thereof is not limited thereto.

The herbicide may include a carrier, a surfactant, a dispersant, or an adjuvant, which are commonly used in formulating agricultural pesticides. The herbicide may be used in an aqueous formulation, an emulsifiable concentrate formulation, a powder formulation, a suspension formulation, or a liquid formulation, but the formulation for the herbicide is not limited thereto. The herbicide may be directly used, or diluted in an appropriate medium before use. A spray amount of the herbicide may be hundreds to thousands liters per hectare (ha), but is not limited thereto. The herbicide may include a surfactant in an amount of about 0.1 to 20 wt %, or a solid or liquid diluent in an amount of 0 to 99.9 wt %, but the amounts of the surfactant and the diluent are not limited thereto.

In an embodiment, the phenylisoxazoline-based compound, or the racemate or enantiomer thereof may be used alone, or together with a herbicidal compound, a safener, a synergistic agent, or a plant growth regulator. The herbicidal compound may include at least one selected from an acetyl-CoA carboxylase (ACC) inhibitor, an acetolactate synthase (ALS) inhibitor, amide, auxinic herbicide, an auxin transport inhibitor, a carotenoid biosynthesis inhibitor, an enolpyruvylshikimate-3-phosphate synthase (ESPS) inhibitor, a glutamine synthetase inhibitor, a lipid biosynthesis inhibitor, a mitosis inhibitor, a protoporphyrinogen IX oxidase inhibitor, a photosynthesis inhibitor, a cell-wall biosynthesis inhibitor, and other herbicides. However, various other materials may also be used together with the phenylisoxazoline-based compound, or the racemate or enantiomer thereof.

Another aspect of the present invention provides a method of preparing the isoxazoline-based compound represented by Formula 1 by a reaction of compounds represented by Formulae 3 and 4 or a reaction of compounds represented by Formulae 5 and 6:

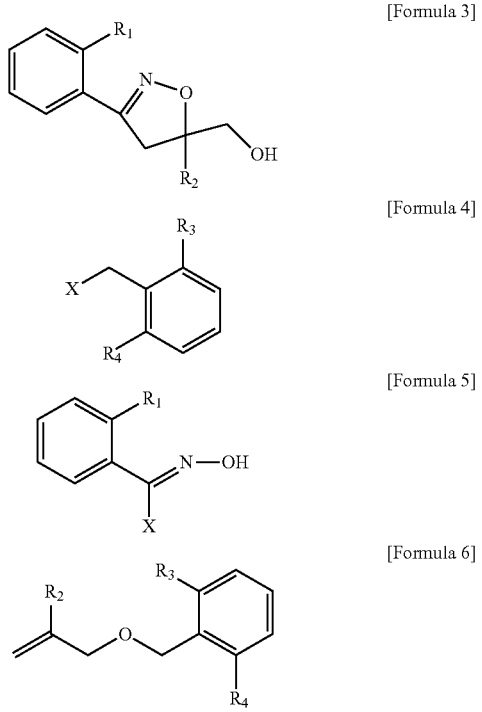

[Formula 3]

[Formula 4]

[Formula 5]

[Formula 6]

in Formulae 3 to 6, $R_1$, $R_2$, $R_3$, and $R_4$ are the same as explained in connection with Formula 1, and X indicates chlorine or bromine.

The compound represented by Formula 1 may be prepared according to Reaction Scheme 1 below. In detail, a hydroxy compound represented by Formula 3 is reacted with a compound represented by Formula 4 in a base condition to obtain the compound represented by Formula 1.

[Reaction Scheme 1]

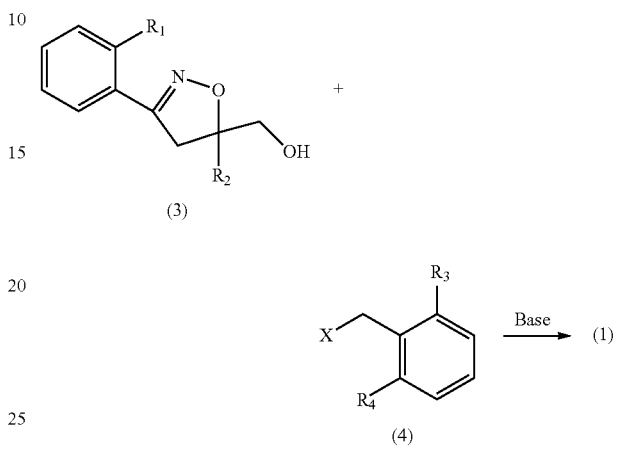

In Reaction Scheme 1, $R_1$, $R_2$, $R_3$, and $R_4$ are the same as explained in connection with Formula 1, and X indicates chlorine or bromine.

In Reaction Scheme 1, when NaOH or KOH is used as a base, the base may be excessively used with respect to the hydroxyl compound of Formula 3 in a mixed solvent of water and an organic solvent, and examples of the organic solvent used herein are toluene, dioxane, tetrahydrofuran, and 1,2-dichloroethane. The reaction may be promoted by adding a phase-transition catalyst to the reaction mixture. Examples of the phase-transition catalyst are tetrabutylammonium bromide, tetramethylammonium bromide, tetraethylammonium bromide, tetrabutylammonium iodide, and tetrabutylammonium hydrogen sulfate. In this regard, the compound of Formula 4 may be used in an amount of 1 to 1.5 mol based on the hydroxy compound of Formula 3, and the reaction may be performed at a temperature of 50 to 100° C. When the reaction stops, the reaction solution is cooled, and a separated organic layer is washed with water, and then, dried and concentrated, followed by refining through column chromatography. Also, when in Reaction Scheme 1, metalhydride, metalamide, metalalkylamide and alkylmetal are used as a base, an available solvent herein may be anhydrous tetrahydrofuran anhydrous dimethylformamide, or anhydrous toluene. In this regard, an amount of the base may be, based on the hydroxy compound of Formula 3, in a range of 1.0 to 1.2 e.q., and an amount of the compound of Formula 4 may be in a range of 1.0 to 1.5 e.q. The reaction temperature may be in a range of −50 to 30° C. When the reaction stops, the reaction product is quenched by using an ammonium chloride aqueous solution, and then, diluted by using an organic solvent to separate an organic layer. The separated organic layer is washed with water, and then, dried and concentrated, followed by refining through column chromatography.

The hydroxy compound of Formula 3 may be prepared as illustrated in Reaction Scheme 2 below:

[Reaction Scheme 2]

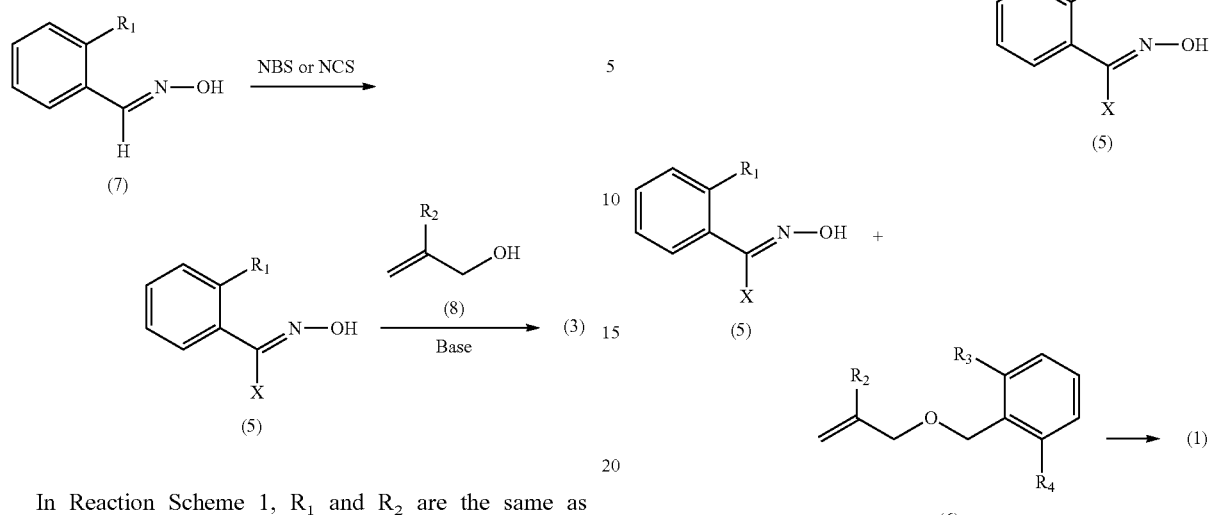

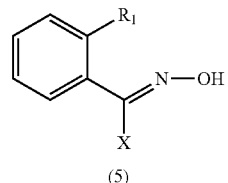

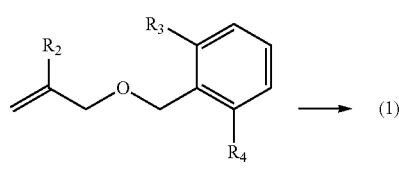

In Reaction Scheme 1, $R_1$ and $R_2$ are the same as explained in connection with Formula 1, and X indicates chlorine or bromine.

In Reaction Scheme 2, the oxime compound (Formula 7) is reacted with 1.0 to 1.2 e.q. of N-bromosuccinimide (NBS) or N-chlorosuccinimide (NCS) in an organic solvent, such as dichloromethane, dichloroethane, toluene, dioxane, or tetrahydrofuran at a temperature of −20 to 30° C. to prepare a halo-oxime compound (Formula 5), and the obtained halo-oxime compound (Formula 5) is reacted with an unsaturated alcohol compound (Formula 8) in an amount of 1.0 to 1.3 e.q. based on the oxime compound (Formula 7) in an organic solvent, such as dichloromethane, dichloroethane, toluene, dioxane, or tetrahydrofuran at a temperature of 0 to 80° C. to obtain a hydroxy compound (Formula 3). The base may include an inorganic salt, such as $NaHCO_3$, $KHCO_3$, $Na_2CO_3$, or $K_2CO_3$, or an organic salt, such as a trialkylamine or a pyridine. An amount of the base may be in a range of 1.0 to 1.5 e.q. based on the oxime compound (Formula 7). To promote the reaction, a phase-change catalyst may be further used, and examples of the phase-change catalyst are tetrabutyl ammoniumbromide, tetramethylammoniumbromide, tetraethylammoniumbromide, tetrabutylammonium iodide, and tetrabutylammonium hydrogensulfate, and an amount of the phase-change catalyst may be in a range of 0.01 to 0.1 e.q. When the reaction stops, the reaction solution i added to an aqueous solution, and an organic layer obtained by extracting with an organic solvent is dried and concentrated and refined by column chromatography.

According to another embodiment, the compound represented by Formula 1 may be prepared according to Reaction Scheme 3 below:

[Reaction Scheme 3]

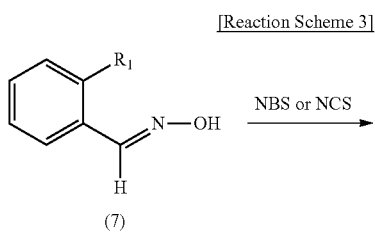

In Reaction Scheme 3, the oxime compound (Formula 7) is reacted with 1.0 to 1.2 e.q. of N-bromosuccinimide (NBS) or N-chlorosuccinimide (NCS) in an organic solvent, such as dichloromethane, dichloroethane, toluene, dioxane, or tetrahydrofuran at a temperature of −20 to 30° C. to prepare a halo-oxime compound (Formula 5), and the obtained halo-oxime compound (Formula 5) is reacted with an unsaturated compound (Formula 6) in an amount of 1.0 to 1.3 e.q. based on the oxime compound (Formula 7) in an organic solvent, such as dichloromethane, dichloroethane, toluene, dioxane, or tetrahydrofuran at a temperature of 0 to 80° C. to obtain an isoxazoline compound (Formula 1). The base may include an inorganic salt, such as $NaHCO_3$, $KHCO_3$, $Na_2CO_3$, or $K_2CO_3$, or an organic salt, such as a trialkylamine or a pyridine. An amount of the base may be in a range of 1.0 to 1.5 e.q. based on the oxime compound (Formula 7). To promote the reaction, a phase-change catalyst may be further used, and examples of the phase-change catalyst are tetrabutyl ammoniumbromide, tetramethylammoniumbromide, tetraethylammoniumbromide, tetrabutylammonium iodide, and tetrabutylammonium hydrogensulfate, and an amount of the phase-change catalyst may be in a range of 0.01 to 0.1 e.q. When the reaction stops, the reaction solution is added to an aqueous solution, and an organic layer obtained by extracting with an organic solvent is dried and concentrated and refined by column chromatography.

Hereinafter, embodiments of the present invention will be described. However, the following embodiments are provided herein for illustrative purpose only, and do not limit the scope of the present invention.

Example 1

Synthesis of 5-((2,6-difluorobenzyloxy)methyl)-5-methyl-3-o-tolyl-4,5-dihydroisoxazole (Compound 1)

60 g of 2-methylbenzaldehyde oxime was dissolved in 1 L of dichloroethane, and then, 65 g of N-chlorosuccinimide and 100 mL of dimethylformamide were slowly added thereto at a temperature of 0° C. The reaction mixture was stirred at room temperature for 1 hour, and then, the reaction state was confirmed by thin layer chromatography (TLC). When 2-methylbenzaldehyde oxime, which was a starting material, disappeared, the reaction mixture was cooled to a temperature of 0° C., and then 56 g of NaHCO$_3$ and 41 mL of 2-methyl-2-propene-1-ol were sequentially added thereto. The reaction mixture was stirred at room temperature overnight, and then washed with water, and then, an separated organic layer was dried and concentrated by using magnesium sulfate, and then, purified by column chromatography to obtain 70 g of (5-methyl-3-o-tolyl-4,5-dihydroisoxazole-5-yl)methanol. The obtained compound was dissolved in 1 L of toluene, and then, 1 L of water, 90 g of NaOH, and 4.5 g of tetrabutylammonium hydrogensulfate were added thereto. After the reaction mixture was stirred for 30 minutes at room temperature, 77 g of 2,6-difluorobenzyl chloride was slowly dropped thereto. The reaction mixture was stirred at a temperature of 60° C. for 5 hours and cooled, and then, a separated organic layer was washed with water and then dried by using magnesium sulfate and concentrated, and the concentrate was separated by silicagel column chromatography to obtain 88 g of 5-((2,6-difluorobenzyloxy)methyl)-5-methyl-3-o-tolyl-4,5-dihydroisoxazole.

Example 2

Synthesis of 3-(2-chlorophenyl)-5-((2,6-difluorobenzyloxy)methyl)-5-methyl-4,5-dihydroisoxazole (Compound 2)

224 mg of 2-chlorobenzaldehyde oxime was dissolved in 4 mL of 1,2-dichloroethane, and then, 230 mg of N-chlorosuccinimide and 0.4 mL of dimethylformamide were slowly added thereto at a temperature of 0° C. The reaction mixture was stirred at room temperature for 1 hour, and then, the reaction state was confirmed by TLC. When the oxime, which was a starting material, disappeared, the reaction mixture was cooled to a temperature 0° C., and then, 182 mg of NaHCO$_3$, 27 mg of tetrabutylammonium iodide, and 342 mg of 1,3-difluoro-2-((2-methylallyloxy)methyl)benzene were sequentially, slowly added thereto. The reaction mixture was stirred at room temperature overnight, and then, diluted with dichloromethane and then washed with water, and the obtained organic layer was dried by using magnesium sulfate and concentrated, and the concentrate was separated by silicagel column chromatography to obtain 400 mg of 3-(2-chlorophenyl)-5-((2,6-difluorobenzyloxy)methyl)-5-methyl-4,5-dihydroisoxazole.

Example 3

Synthesis of 3-(2-bromophenyl)-5-((2,6-difluorobenzyloxy)methyl)-5-methyl-4,5-dihydroisoxazole (Compound 3)

287 mg of 2-bromobenzaldehyde oxime was dissolved in 4 mL of 1,2-dichloroethane, and then, 230 mg of N-chlorosuccinimide and 0.4 mL of dimethylformamide were slowly added thereto at a temperature of 0° C. The reaction mixture was stirred at room temperature for 1 hour, and then, the reaction state was confirmed by TLC. When the oxime, which was a starting material, disappeared, the reaction mixture was cooled to a temperature 0° C., and then, 182 mg of NaHCO$_3$, 27 mg of tetrabutylammonium iodide, and 342 mg of 1,3-difluoro-2-((2-methylallyloxy)methyl)benzene were sequentially, slowly added thereto. The reaction mixture was stirred at room temperature overnight, and then, diluted with dichloromethane, and then, washed with water, and the obtained organic layer was dried by using magnesium sulfate and concentrated, and the concentrate was separated by silicagel column chromatography to obtain 450 mg of 3-(2-bromophenyl)-5-((2,6-difluorobenzyloxy)methyl)-5-methyl-4,5-dihydroisoxazole.

Example 4

Synthesis of 5-((2,6-difluorobenzyloxy)methyl)-3-(2-fluorophenyl)-5-methyl-4,5-dihydroisoxazole (Compound 4)

200 mg of 2-fluorobenzaldehyde oxime was dissolved in 4 mL of 1,2-dichloroethane, and then, 230 mg of N-chlorosuccinimide and 0.4 mL of dimethylformamide were slowly added thereto at a temperature of 0° C. The reaction mixture was stirred at room temperature for 1 hour, and then, the reaction state was confirmed by TLC. When the oxime, which was a starting material, disappeared, the reaction mixture was cooled to a temperature 0° C., and then, 182 mg of NaHCO$_3$, 27 mg of tetrabutylammonium iodide, and 342 mg of 1,3-difluoro-2-((2-methylallyloxy)methyl)benzene were sequentially, slowly added thereto. The reaction mixture was stirred at room temperature overnight, and then, diluted with dichloromethane, and then, washed with water, and the obtained organic layer was dried by using magnesium sulfate and concentrated, and the concentrate was separated by silicagel column chromatography to obtain 385 mg of 5-((2,6-difluorobenzyloxy)methyl)-3-(2-fluorophenyl)-5-methyl-4,5-dihydroisoxazole.

Example 5

Synthesis of 5-((2,6-difluorobenzyloxy)methyl)-5-methyl-3-(2-(trifluoromethyl)phenyl)-4,5-dihydroisoxazole (Compound 5)

223 mg of 2-trifluoromethylbenzaldehyde oxime was dissolved in 4 mL of 1,2-dichloroethane, and then, 230 mg of N-chlorosuccinimide and 0.4 mL of dimethylformamide were slowly added thereto at a temperature of 0° C. The reaction mixture was stirred at room temperature for 1 hour, and then, the reaction state was confirmed by TLC. When the oxime, which was a starting material, disappeared, the reaction mixture was cooled to a temperature 0° C., and then, 182 mg of NaHCO$_3$, 27 mg of tetrabutylammonium iodide, and 342 mg of 1,3-difluoro-2-((2-methylallyloxy)methyl)benzene were sequentially, slowly added thereto. The reaction mixture was stirred at room temperature overnight, and then, diluted with dichloromethane, and then, washed with water, and the obtained organic layer was dried by using magnesium sulfate and concentrated, and the concentrate was separated by silicagel column chromatography to obtain 410 mg of 5-((2,6-difluorobenzyloxy)methyl)-5-methyl-3-(2-(trifluoromethyl)phenyl)-4,5-dihydroisoxazole.

One of ordinary skill in the art may prepare compounds shown in Table 1 by directly or indirectly using synthesis methods illustrated in the examples without any undue difficulties.

TABLE 1

List of Compounds 1 to 5 synthesized according to Examples 1 to 5

| Compound | Structure | $^1$H NMR(CDCl$_3$)δ |
|---|---|---|
| 1 | (2-methylphenyl isoxazoline with 2,6-difluorobenzyloxymethyl) | 7.32-7.18(m, 5H), 6.90(d, J = 7.5 Hz, 1H), 6.86(d, J = 8.2 Hz, 1H), 4.71(s, 2H), 3.61(d, J = 9.9 Hz, 1H), 3.53(d, J = 9.9 Hz, 1H), 3.46(d, J = 16.7 Hz, 1H), 3.00(d, J = 16.7 Hz, 1H), 2.52(s, 3H), 1.46(s, 3H) |
| 2 | (2-chlorophenyl isoxazoline with 2,6-difluorobenzyloxymethyl) | 7.83(t, J = 7.6 Hz, 1H), 7.40-7.21(m, 2H), 7.15(t, J = 7.7 Hz, 1H), 7.09(dd, J = 8.3 Hz, J = 11.3 Hz, 1H), 6.88(t, J = 7.6 Hz, 2H), 4.70(s, 1H), 3.59(d, J = 10.0 Hz, 1H), 3.56(d, J = 10.0 Hz, 1H), 3.47 (d, J = 17.4 Hz, 1H), 3.07(d, J = 17.4 Hz, 1H), 1.45 (s, 3H) |
| 3 | (2-bromophenyl isoxazoline with 2,6-difluorobenzyloxymethyl) | 7.58(d, J = 7.9 Hz, 1H), 7.46(d, J = 7.6 Hz, 1 H), 7.34-7.20(m, 3H), 6.88(t, J = 7.5 Hz, 2H), 4.71(s, 1H), 3.64(d, J = 9.9 Hz, 1H), 3.53(d, J = 9.9 Hz, 1H), 3.52(d, J = 17.1 Hz, 1H), 3.11(d, J = 17.1 Hz, 1H), 1.49(s, 3H) |
| 4 | (2-fluorophenyl isoxazoline with 2,6-difluorobenzyloxymethyl) | 7.58(d, J = 7.4 Hz, 1H), 7.38-7.24(m, 4H), 6.88(t, J = 7.6 Hz, 2H), 4.71(s, 1 H), 4.63(d, J = 9.9 Hz, 1H), 3.53(d, J = 9.9 Hz, 1H), 3.52(d, J = 17.1 Hz, 1H), 3.13(d, J = 17.1 Hz, 1H), 1.49(s, 3H) |
| 5 | (2-trifluoromethylphenyl isoxazoline with 2,6-difluorobenzyloxymethyl) | $^1$H NMR(CDCl$_3$, 300 MHz) δ 1.47(s, 3H), 2.97(d, 1H, J = 17.19 Hz), 3.38 (d, 1H, J = 17.19 Hz), 3.58(dd, 2H, J = 9.96, 9.93 Hz), 4.74(d, 1H, J = 2.79), 6.90(t, 2H, J = 7.44, 8.19 Hz), 7.29(m, 1H), 7.59(m, 3H), 7.72(m, 1H) |

Example 6

Choosing Reference Compounds

The present experiment was performed to confirm weed control effects of the compounds according to embodiments of the present invention. First, activities of Compounds 1 to 5 represented by Formula 1 were compared with activities of isoxazoline-based compounds of preceding patents or materials which are included in the scope of claims of preceding patents and of which change in $R_1$ and $R_3$/$R_4$ substituents in Formula 1 is outside the scope of the claims of the present invention, by using Compounds A to H as a reference compound (Table 2). Reference A is disclosed in U.S. Pat. No. 5,262,388, and References B and H are disclosed in U.S. Pat. No. 4,983,210. References C to G are included in the scope of claims of U.S. Pat. No. 4,983,210 while $R_1$ or $R_3$ and $R_4$ substituents of Formula 1 are not included in the scope of claims of the present invention. Reference compounds were synthesized by using methods similar to those used in examples used herein, and $^1$H NMR of synthesized reference compounds is shown in Table 3 below.

TABLE 2

List of reference compounds

| Reference compound | Structure | Reasons for Choosing |
|---|---|---|
| A | (2-nitrophenyl isoxazoline with 2-fluorobenzyloxymethyl) | Disclosed in U.S. Pat. No. 5,262,388 |

TABLE 2-continued

List of reference compounds

| Reference compound | Structure | Reasons for Choosing |
|---|---|---|
| B | (2-chlorophenyl isoxazoline with 2,6-dichlorofluorobenzyl ether) | Disclosed in U.S. Pat. No. 4,983,210 |
| C | (2-methylphenyl isoxazoline with benzyl ether) | To compare activity change when 2, 6 substituents of a benzyl group are not simultaneously fluorine (novel synthesis) |
| D | (2-methylphenyl isoxazoline with 2-fluorobenzyl ether) | To compare activity change when 2, 6 substituents of a benzyl group are not simultaneously fluorine (novel synthesis) |
| E | (2-methylphenyl isoxazoline with 2-fluoro-6-chlorobenzyl ether) | To compare activity change when 2, 6 substituents of a benzyl group are not simultaneously fluorine (novel synthesis) |
| F | (3-methylphenyl isoxazoline with 2,6-difluorobenzyl ether) | To compare activity change when a phenyl isoxazoline does not have 2(ortho)-substituent (novel synthesis) |
| G | (4-methylphenyl isoxazoline with 2,6-difluorobenzyl ether) | To compare activity change when a phenyl isoxazoline does not have a 2(ortho)-substituent (novel synthesis) |
| H | (phenyl isoxazoline with 2-fluoro-6-chlorobenzyl ether) | To compare activity change when a phenyl isoxazoline does not have a 2(ortho)-substituent (disclosed in U.S. Pat. No. 4,983,210) |

TABLE 3

$^1$H NMR of reference compounds

| Reference compound | $^1$H NMR |
|---|---|
| A | (500 MHz, CDCl$_3$) δ 8.05(d, J = 8.2 Hz, 1H), 7.67(t, J = 7.6 Hz, 1H), 7.61(d, J = 7.9 Hz, 1H), 7.57(d, J = 7.6 Hz, 1H), 7.45(t, J = 7.5 Hz, 1H), 7.31(m, 1H), 7.15(t, J = 7.5 Hz, 1H), 7.06(t, J = 9.0 Hz, 1H), 4.73(q, J = 10.5 Hz, 2H), 3.71(d, J = 10.1 Hz, 1H), 3.61(d, J = 10.1 Hz, 1H), 3.35(d, J = 16.7 Hz, 1H), 2.99(d, J = 16.7 Hz, 1H), 1.56(s, 3H) |
| B | (300 MHz, CDCl$_3$) δ 7.58(d, J = 7.3 Hz, 1H), 7.40(t, J = 7.7 Hz, 1H), 7.35-7.18(m, 4H), 6.99(t, J = 7.3 Hz, 1H), 4.78(s, 2H), 3.64(d, J = 10.0 Hz, 1H), 3.56(d, J = 17.1 Hz, 1H), 3.54(d, J = 10.0 Hz, 1H), 3.13(d, J = 17.1 Hz, 1H), 1.48(s, 3H) |

TABLE 3-continued

¹H NMR of reference compounds

| Reference compound | ¹H NMR |
|---|---|
| C | (300 MHz, CDCl₃) δ 7.34-7.19(m, 9H), 4.62(s, 2H), 3.58(d, J = 10.0 Hz, 1H), 3.52(d, J = 10.0 Hz, 1H), 3.50(d, J = 16.6 Hz, 1H), 3.05(d, J = 16.6 Hz, 1H), 2.54(s, 3H), 1.48(s, 3H) |
| D | (300 MHz, CDCl₃) δ 7.40(t, J = 7.3 Hz, 1H), 7.31-7.19(m, 5H), 7.11(t, J = 7.5 Hz, 1H), 7.00(t, J = 8.6 Hz, 1H), 4.68(s, 2H), 3.63(d, J = 10.0 Hz, 1H), 3.56(d, J = 10.0 Hz, 1H), 3.50(d, J = 16.7 Hz, 1H), 3.06(d, J = 16.7 Hz, 1H), 2.54(s, 3H), 1.49(s, 3H) |
| E | (300 MHz, CDCl₃) δ7.30-7.17(m, 6H), 6.99(t, J = 9.1 Hz, 1H), 4.77(s, 2H), 3.63(d, J = 9.8 Hz, 1H), 3.54(d, J = 9.8 Hz, 1H), 3.50(d, J = 16.7 Hz, 1H), 3.01(d, J = 16.7 Hz, 1H), 2.52(s, 3H), 1.47(s, 3H) |
| F | (300 MHz, CDCl₃) δ7.48(s, 1H), 7.42(d, J = 7.6 Hz, 1H), 7.31-7.18(m, 3H), 6.88(t, J = 8.2 Hz, 2H), 4.70(s, 2H), 3.69(d, J = 9.8 Hz, 1H), 3.52(d, J = 9.8 Hz, 1H), 2.95(d, J = 16.7 Hz, 1H), 3.01(d, J = 16.7 Hz, 1H), 2.37(s, 3H), 1.45(s, 3H) |
| G | (300 MHz, CDCl₃) δ7.52(d, J = 8.2 Hz, 2H), 7.25(m, 1H), 7.18(d, J = 8.0 Hz, 2H), 6.87(t, J = 8.2 Hz, 2H), 4.69(s, 2H), 3.58(d, J = 9.8 Hz, 1H), 3.52(d, J = 9.8 Hz, 1H), 3.39(d, J = 16.7 Hz, 1H), 2.94(d, J = 16.7 Hz, 1H), 2.36(s, 3H), 1.44(s, 3H) |
| H | (300 MHz, CDCl₃) δ7.65(d, J = 5.6 Hz, 1H), 7.64(t, J = 6.7 Hz, 1H), 7.42-7.37(m, 3H), 7.27-7.17(m, 2H), 6.99(t, J = 8.6 Hz, 1H), 4.76(s, 2H), 3.61(d, J = 9.8 Hz, 1H), 3.54(d, J = 9.8 Hz, 1H), 3.46(d, J = 16.7 Hz, 1H), 2.96(d, J = 16.7 Hz, 1H), 1.46(s, 3H) |

Example 7

Pre-Emergence Treatment

A rectangular plastic pot having a surface area of 300 cm² was filled with sandy loam soil and mixed bed soil which were mixed at a ratio of 1:1, and then, barnyardrass (*Echinochloa crusgalli*), large crabgrass (*Digitaria sanguinalis*), blackgrass (*Alopecurus myosuroides*), and annual bluegrass (*Poa annua*), which are grass weeds, were seeded thereto. In a pot that was prepared as described above, seeds of corn, soybean, cotton, wheat, and rice were seeded. The pots were irrigated, and one day after, chemicals were sprayed thereto. The spraying was performed by using a track sprayer (R&D Sprayer, USA) equipped with a Teejet 8002 (Spraying Systems Co., USA) nozzle, and a spraying amount was adjusted at 300 L/ha. A spraying solution was prepared by dissolving test materials or references in acetone and adding the same amount of 0.2%(v/v) tween 20 aqueous solution thereto. Application rates were 500, 250, 125, and 62.5 g/ha. The pots were placed in a greenhouse in which during day, the temperature was maintained at a temperature of 25 to 30° C., and during night, the temperature was maintained at a temperature of 15 to 25° C., and the pots were periodically irrigated. Four weeks after the spraying the test materials or References, effects and phytotoxicity of the respective weeds and crops were evaluated in a scale of 0 to 10 (0: no effects, 10: complete death), and results thereof are shown in Table 4 below.

TABLE 4

Phytotoxcity and herbicidal efficacy of the test materials and references by pre-emergence treatment

| Compound | Rate (g/ha) | Crops | | | | | Weeds | | | |
|---|---|---|---|---|---|---|---|---|---|---|
| | | Corn | Soybean | Cotton | Wheat | Rice | Echinochloa crusgalli | Digitaria sanguinalis | Poa annua | Alopecurus myosuroides |
| 1 | 500 | 1 | 0 | 0 | 0 | 0 | 10 | 10 | 10 | 9 |
| | 250 | | | | | | 10 | 10 | 10 | 8 |
| | 125 | | | | | | 10 | 10 | 10 | 6 |
| | 62.5 | | | | | | 10 | 9 | 9 | 4 |
| 2 | 500 | 0 | 0 | 0 | 0 | 0 | 10 | 10 | 10 | 10 |
| | 250 | | | | | | 10 | 10 | 10 | 6 |
| | 125 | | | | | | 10 | 10 | 9 | 3 |
| | 62.5 | | | | | | 9 | 9 | 8 | 2 |
| 3 | 500 | 2 | 0 | 0 | 0 | 0 | 10 | 10 | 10 | 7 |
| | 250 | | | | | | 10 | 10 | 8 | 5 |
| | 125 | | | | | | 10 | 10 | 7 | 4 |
| | 62.5 | | | | | | 10 | 10 | 4 | 4 |
| 4 | 500 | 4 | 0 | 1 | 0 | 0 | 10 | 10 | 10 | 10 |
| | 250 | | | | | | 10 | 10 | 10 | 8 |
| | 125 | | | | | | 10 | 10 | 10 | 4 |
| | 62.5 | | | | | | 7 | 10 | 9 | 3 |
| 5 | 500 | 3 | 2 | 1 | 0 | 0 | 10 | 10 | 10 | 8 |
| | 250 | | | | | | 10 | 10 | 9 | 7 |
| | 125 | | | | | | 10 | 10 | 9 | 6 |
| | 62.5 | | | | | | 10 | 10 | 9 | 5 |
| A | 500 | 0 | 0 | 0 | 0 | 0 | 10 | 10 | 9 | 10 |
| | 250 | | | | | | 6 | 6 | 5 | 3 |

TABLE 4-continued

Phytotoxcity and herbicidal efficacy of the test materials and references by pre-emergence treatment

| Compound | Rate (g/ha) | Crops | | | | | Weeds | | | |
|---|---|---|---|---|---|---|---|---|---|---|
| | | Corn | Soybean | Cotton | Wheat | Rice | Echinochloa crusgalli | Digitaria sanguinalis | Poa annua | Alopecurus myosuroides |
| | 125 | | | | | | 2 | 2 | 2 | 0 |
| | 62.5 | | | | | | 0 | 0 | 0 | 0 |
| B | 500 | 0 | 0 | 0 | 0 | 0 | 10 | 9 | 10 | 10 |
| | 250 | | | | | | 7 | 8 | 8 | 3 |
| | 125 | | | | | | 5 | 4 | 4 | 0 |
| | 62.5 | | | | | | 2 | 0 | 2 | 0 |
| C | 500 | 1 | 1 | 1 | 0 | 0 | 10 | 10 | 9 | 6 |
| | 250 | | | | | | 8 | 9 | 9 | 4 |
| | 125 | | | | | | 5 | 6 | 5 | 2 |
| | 62.5 | | | | | | 2 | 0 | 2 | 0 |
| D | 500 | 0 | 0 | 0 | 0 | 0 | 10 | 10 | 8 | 9 |
| | 250 | | | | | | 6 | 6 | 5 | 3 |
| | 125 | | | | | | 3 | 2 | 2 | 0 |
| | 62.5 | | | | | | 1 | 0 | 0 | 0 |
| E | 500 | 0 | 0 | 0 | 0 | 0 | 10 | 10 | 10 | 9 |
| | 250 | | | | | | 8 | 9 | 9 | 4 |
| | 125 | | | | | | 5 | 5 | 5 | 0 |
| | 62.5 | | | | | | 2 | 0 | 2 | 0 |
| F | 500 | 1 | 0 | 0 | 0 | 0 | 10 | 10 | 9 | 3 |
| | 250 | | | | | | 5 | 6 | 5 | 0 |
| | 125 | | | | | | 1 | 2 | 0 | 0 |
| | 62.5 | | | | | | 0 | 1 | 0 | 0 |
| G | 500 | 0 | 0 | 0 | 0 | 0 | 10 | 10 | 9 | 3 |
| | 250 | | | | | | 7 | 8 | 8 | 0 |
| | 125 | | | | | | 3 | 4 | 4 | 0 |
| | 62.5 | | | | | | 0 | 1 | 1 | 0 |
| H | 500 | 2 | 0 | 0 | 0 | 0 | 9 | 10 | 8 | 9 |
| | 250 | | | | | | 2 | 2 | 2 | 2 |
| | 125 | | | | | | 0 | 0 | 0 | 0 |
| | 62.5 | | | | | | 0 | 0 | 0 | 0 |

When Compounds 1 to 5 were used, at the rate of 62.5 to 125 g/ha, grass weeds including barnyardrass, large crabgrass, and annual bluegrass were completely controlled. However, regarding the references, at 500 g/ha, the grass weeds were well controlled, but at 250 g/ha, the efficacy decreased dramatically, and at 125 g/ha or less, efficacy were negligible. Compounds 1 and 5 showed about 8 times stronger efficacy than the References, and Compounds 2 and 4 showed about 4 times as stronger efficacy than the References.

Example 8

Post-Emergence Treatment

Pots containing crops and weeds were prepared in the same manner as in Example 7, and then, in the second week in which crops and weeds entered into about 3 leaf stage, the test materials and the references were sprayed thereto in the same manner as described above. The rates were 1,000, 500, 250, and 125 g/ha. Four weeks after the spraying of the test materials or the references, herbicidal efficacy and phytotoxicity to the respective weeds and crops were evaluated in a scale of 0 to 10 (0: no effects, 10: complete death). Results thereof are shown in Table 5.

TABLE 5

Phytotoxcity and herbicidal efficacy of the test materials and references by post-emergence treatment

| Compound | Rate (g/ha) | Crops | | | | | Weeds | | | |
|---|---|---|---|---|---|---|---|---|---|---|
| | | Corn | Soybean | Cotton | Wheat | Rice | Echinochloa crusgalli | Digitaria sanguinalis | Poa annua | Alopecurus myosuroides |
| 1 | 1,000 | 2 | 2 | 2 | 0 | 0 | 10 | 10 | 10 | 9 |
| | 500 | | | | | | 10 | 10 | 9 | 7 |
| | 250 | | | | | | 9 | 9 | 8 | 8 |
| | 125 | | | | | | 7 | 6 | 5 | 2 |
| 2 | 1,000 | 2 | 1 | 1 | 1 | 1 | 10 | 10 | 10 | 9 |
| | 500 | | | | | | 8 | 6 | 8 | 7 |
| | 250 | | | | | | 5 | 5 | 8 | 5 |
| | 125 | | | | | | 0 | 5 | 5 | 1 |

TABLE 5-continued

Phytotoxcity and herbicidal efficacy of the test materials and references by post-emergence treatment

| Compound | Rate (g/ha) | Crops | | | | | Weeds | | | |
|---|---|---|---|---|---|---|---|---|---|---|
| | | Corn | Soybean | Cotton | Wheat | Rice | Echinochloa crusgalli | Digitaria sanguinalis | Poa annua | Alopecurus myosuroides |
| 4 | 1,000 | 4 | 1 | 0 | 1 | 2 | 10 | 10 | 10 | 10 |
| | 500 | | | | | | 10 | 10 | 10 | 9 |
| | 250 | | | | | | 8 | 6 | 7 | 4 |
| | 125 | | | | | | 5 | 6 | 6 | 0 |
| 5 | 1,000 | 5 | 2 | 0 | 0 | 0 | 10 | 10 | 10 | 9 |
| | 500 | | | | | | 10 | 10 | 8 | 5 |
| | 250 | | | | | | 8 | 8 | 7 | 4 |
| | 125 | | | | | | 6 | 6 | 6 | 1 |
| A | 1,000 | 0 | 1 | 0 | 0 | 0 | 7 | 5 | 5 | 2 |
| | 500 | | | | | | 5 | 4 | 3 | 0 |
| | 250 | | | | | | 2 | 1 | 0 | 0 |
| | 125 | | | | | | 0 | 0 | 0 | 0 |
| B | 1,000 | 0 | 2 | 0 | 0 | 0 | 7 | 8 | 6 | 3 |
| | 500 | | | | | | 1 | 6 | 4 | 0 |
| | 250 | | | | | | 0 | 5 | 1 | 0 |
| | 125 | | | | | | 0 | 0 | 0 | 0 |
| C | 1,000 | 2 | 0 | 0 | 0 | 0 | 7 | 7 | 4 | 5 |
| | 500 | | | | | | 4 | 4 | 3 | 3 |
| | 250 | | | | | | 3 | 3 | 2 | 0 |
| | 125 | | | | | | 1 | 1 | 0 | 0 |
| D | 1,000 | 0 | 0 | 0 | 0 | 0 | 4 | 7 | 5 | 4 |
| | 500 | | | | | | 1 | 4 | 2 | 3 |
| | 250 | | | | | | 0 | 0 | 0 | 0 |
| | 125 | | | | | | 0 | 0 | 0 | 0 |
| E | 1,000 | 3 | 1 | 3 | 0 | 0 | 6 | 7 | 7 | 4 |
| | 500 | | | | | | 5 | 6 | 6 | 2 |
| | 250 | | | | | | 2 | 1 | 2 | 0 |
| | 125 | | | | | | 0 | 0 | 0 | 0 |
| F | 1,000 | 2 | 0 | 0 | 0 | 0 | 6 | 6 | 6 | 4 |
| | 500 | | | | | | 4 | 4 | 5 | 2 |
| | 250 | | | | | | 3 | 3 | 3 | 0 |
| | 125 | | | | | | 0 | 0 | 0 | 0 |
| G | 1,000 | 0 | 2 | 0 | 0 | 0 | 6 | 6 | 6 | 3 |
| | 500 | | | | | | 5 | 4 | 4 | 2 |
| | 250 | | | | | | 2 | 0 | 1 | 0 |
| | 125 | | | | | | 0 | 0 | 0 | 0 |
| H | 1,000 | 0 | 0 | 0 | 0 | 0 | 4 | 5 | 4 | 0 |
| | 500 | | | | | | 0 | 1 | 2 | 0 |
| | 250 | | | | | | 0 | 0 | 0 | 0 |
| | 125 | | | | | | 0 | 0 | 0 | 0 |

Compounds 1, 4, and 5, at 250 g/ha, greatly suppressed barnyardgrass, large crabgrass, and annual bluegrass. However, the references showed insufficient effects even at 1,000 g/ha. The herbicidal efficacy of Compounds 1, 4, and 5 had at least 4 times stronger than that of the references.

Example 9

Structural Activity Relationships of the Compounds of the Present Invention and the Reference Compounds The compound represented by Formula 1 is equivalent to a compound represented by Formula 2a in which $R_1$ is a phenyl substituted with alkyl, halogen, or haloalkyl at an ortho position, and $R_7$ is a phenyl substituted with fluorines at 2,6-positions.

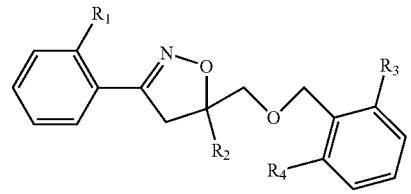

[Formula 1]

wherein, $R_1$ indicates a $C_1$ to $C_4$ alkyl group, a halogen group, or a haloalkyl group, $R_2$ indicates a hydrogen, a methyl group, or an ethyl group, and $R_3$ and $R_4$ each indicates a fluorine.

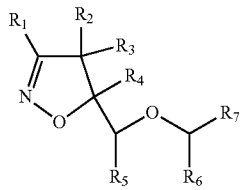

[Formula 2a]

As illustrated in Examples 7 and 8, it was confirmed that a compound represented by Formula 1 in which $R_1$ is alkyl, halogen or haloalkyl at a 2(ortho)-position and $R_3$ and $R_4$ are all fluorine, has at least 8 times (pre-emergence treatment) or 4-times (post-emergence treatment) stronger efficacy than other compounds which do not comply with these two conditions. The other compounds include a phenylisoxazoline derivative that is not substituted (substituted with a hydrogen); a phenylisoxazoline derivative that is substituted at other positions than 2(ortho)-position (controls H, F and G), or an isoxazoline derivative including a benzyl group that is not simultaneously substituted with fluorine at 2,6-positions (control B, C, D and E). These materials have much lower activity than compounds of Formula 1.

In Examples 7 and 8, after the chemical treatment, the references also showed relatively high herbicidal activity up until about 2 weeks. However, thereafter, weeds were rapidly recovered and the efficacy rapidly decreased. On the other hand, the compounds according to the present invention retain their effects even after 2 weeks, and thus, showed higher efficacy eventually.

From the structural activity relationships, although a compound represented by Formula 1 in which $R_1$ is alkyl, halogen or haloalkyl in the 2 (ortho) position, and $R_3$ and $R_4$ are all fluorine, is within the scope of Formula 2a, no examples were provided in any preceding patent; and it was confirmed that the compounds in the present invention are specifically higher in efficacy compared to other disclosed examples in Formula 2a. In consideration of typical isoxazoline-based materials showing their activity at as high as about 1 kg/ha and thus having low economic efficiency, if the compound according to the present invention has high efficiency so that only an amount of 250 g/ha or less is required, economic efficiency would be substantially better, and thus, possibility for commercial availability is high. The specific new compounds exemplified in the present invention have substantially higher efficiency than other isoxazoline-based compounds; and due to such high efficiency, the new compounds would have a high possibility of commercialization.

Whether preceding patents disclose such structural specificity is described in detail as follows. While U.S. Pat. No. 4,983,210 claims Formula 2a in which $R_1$ of Formula 2a is a substituted or unsubstituted phenyl, it does not provide any difference in activity between a substituted phenyl and unsubstituted phenyl, or any change in activity according to a presence or position of substituent. Likewise, when $R_7$ is claimed as a substituted or unsubstituted phenyl, U.S. Pat. No. 4,983,210 fails to disclose difference in activity between a substituted and unsubstituted phenyl, or any change in activity according to a presence or position of substituent. Further, it is not possible to predict a combined effect of $R_1$ and $R_7$ in efficacy.

While U.S. Pat. No. 5,262,388 claimed Formula 2b, wherein X is nitro, there is no indication of activity difference according to the position of substitution among 2, 3, or 4-position in the phenyl ring. In addition, while Y was claimed to be hydrogen or halogen, there was no difference in activity according to the kind or position of the substituent. Therefore, U.S. Pat. No. 5,262,388 does not provide any clue or information that the compounds in the present invention, in which only when in Formula 1, $R_1$ is alkyl, halogen, or haloalkyl at the 2 (ortho) position, and at the same time, $R_3$ and $R_4$ are both fluorine, have high herbicidal effects.

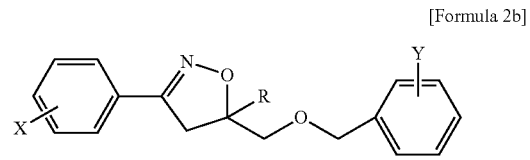

[Formula 2b]

a. While Japanese Patent Publication No. 1997-143171 claims Formula 2c in which $R_3$ is a substituted aryl group, it does not provide any information when $R_3$ and $R_4$ in Formula 1 are simultaneously fluorine, the efficacy become higher.

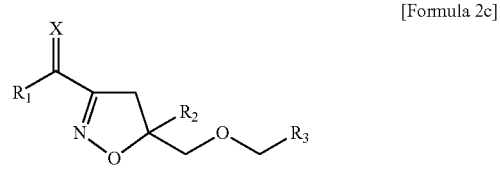

[Formula 2c]

While Japanese Patent Publication No. 2001-158787 claims Formula 2d in which $R_8$ of Formula 2d is a hydrogen, haloalkyl, haloalkenyl, or a substituted aryl, it does not provide any information useful to predict structure-activity relation according to the kind or position of substituent in the phenyl ring.

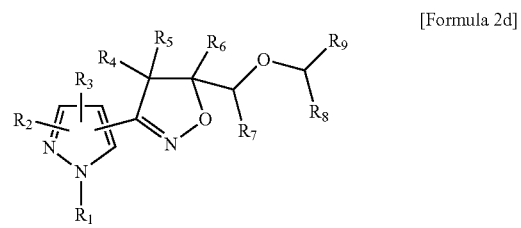

[Formula 2d]

While U.S. Pat. No. 6,838,416 discloses thiophene isoxazoline compounds represented by Formula 2e in which $Y_1$, $Y_2$, and $Y_3$ are each a hydrogen or a fluorine atom, it does not describe specific structure-activity relationship according to the kind or position of the substituent.

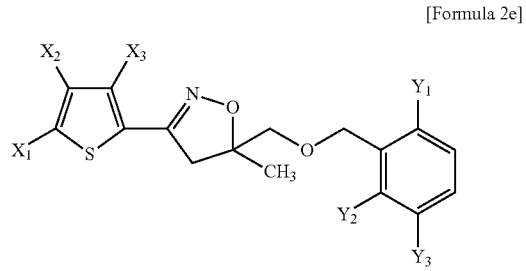

[Formula 2e]

Collectively, the preceding patents fail to disclose any information supporting the present finding that only when, in Formula 1, $R_1$ is alkyl, halogen or haloalkyl in the 2-position, and at the same time, $R_3$ and $R_4$ are both fluorine, a high herbicidal activity is obtained. Therefore, the specific structure-activity relationship exemplified in the present invention is a complete new feature.

The invention claimed is:

1. A method of selectively controlling grass weed, wherein the grass weed is *Echinochloa crusgalli, Digitaria sanguinalis, Alopecurus myosuroides, Poa annua*, the method comprising: treating with an ortho-substituted phenylisoxazoline-based compound represented by Formula I, or a racemate or enantiomer thereof:

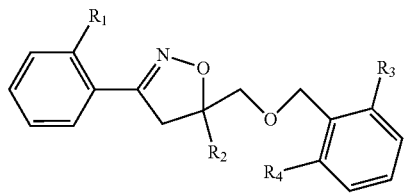

Formula I wherein, $R_1$ indicates a $C_1$ to $C_4$ alkyl group, a halogen group, or a haloalkyl group; $R_2$ indicates a hydrogen, a methyl group, or an ethyl group; and $R_3$ and $R_4$ each indicates a fluorine.

2. The method of claim 1, wherein the treatment is performed before the grass weed emerges.

3. The method of claim 1, wherein the treatment is performed after the grass weed emerges.

4. The method of claim 1, wherein the grass weed is *Echinochloa crusgalli*.

5. The method of claim 1, wherein the grass weed is *Digitaria sanguinalis*.

6. The method of claim 1, wherein the grass weed is *Alopecurus myosuroides*.

7. The method of claim 1, wherein the grass weed is *Poa annua*.

8. The method of claim 1, wherein $R_1$ is a methyl group, a fluorine group, a chlorine group, a bromine group, or a trifluoromethyl group.

9. The method of claim 1, wherein the ortho-substituted phenylisoxazoline-based compound, or the racemate or enantiomer thereof is selected from the group consisting of 5-((2,6-difluorobenzyloxy)methyl)-5-methyl-3-O-tolyl-4,5-dihydroisoxazole, 3-(2-chlorophenyl)-5-((2,6-difluorobenzyloxy)methyl)-5-methyl-4,5-dihydroisoxazole, 3-(2-bromophenyl)-5-((2,6-difluorobenzyloxy)methyl)-5-methyl-4,5-dihydroisoxazole, 5-((2,6-difluorobenzyloxy)methyl)-3-(2-fluorophenyl)-5-methyl-4,5-dihydroisoxazole, and 5-((2,6-difluorobenzyloxy)methyl)-5-methyl-3-(2-(trifluoromethyl)phenyl)-4,5-dihydroisoxazole.

10. The method of claim 1, wherein the ortho-substituted phenylisoxazoline-based compound, or the racemate or enantiomer thereof is included in an herbicide as an active ingredient.

11. The method of claim 10, wherein the herbicide comprises the ortho-substituted phenylisoxazoline-based compound, or the racemate or enantiomer thereof as a single active ingredient, in an amount of 0.5 to 80 wt % based on the total weight of the herbicide.

12. The method of claim 10, wherein the herbicide comprises the ortho-substituted phenylisoxazoline-based compound, or the racemate or enantiomer thereof as a single active ingredient, in an amount of 0.5 to 40 wt % based on the total weight of the herbicide.

13. The method of claim 9, wherein the treatment is performed before the grass weed emerges.

14. The method of claim 9, wherein the treatment is performed after the grass weed emerges.

15. The method of claim 9, wherein the grass weed is *Echinochloa crusgalli*.

16. The method of claim 9, wherein the grass weed is *Digitaria sanguinalis*.

17. The method of claim 9, wherein the grass weed is *Alopecurus myosuroides*.

18. The method of claim 9, wherein the grass weed is *Poa annua*.

* * * * *